US006775564B1

(12) United States Patent
Peters et al.

(10) Patent No.: US 6,775,564 B1
(45) Date of Patent: *Aug. 10, 2004

(54) NON-INVASIVE GLUCOSE MEASURING DEVICE AND METHOD FOR MEASURING BLOOD GLUCOSE

(75) Inventors: Richard K. Peters, Tallmadge, OH (US); Donald Elmerick, Tallmadge, OH (US)

(73) Assignee: LifeTrac Systems, Inc., Biddeford, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/367,425

(22) PCT Filed: Jun. 5, 1997

(86) PCT No.: PCT/US97/08852

§ 371 (c)(1),
(2), (4) Date: Aug. 12, 1999

(87) PCT Pub. No.: WO98/36681

PCT Pub. Date: Aug. 27, 1998

Related U.S. Application Data

(63) Continuation-in-part of application No. 08/803,066, filed on Feb. 20, 1997, now Pat. No. 5,910,109.

(51) Int. Cl.[7] ............................................... A61B 5/00
(52) U.S. Cl. ...................................................... 600/316
(58) Field of Search ............................... 600/310, 316, 600/322, 344; 356/39

(56) References Cited

U.S. PATENT DOCUMENTS

| 4,882,492 A | 11/1989 | Schlager |
| 4,901,728 A | 2/1990 | Hutchison |

(List continued on next page.)

FOREIGN PATENT DOCUMENTS

| DE | 3541 165 A1 | 5/1987 |

OTHER PUBLICATIONS

Subcommittee on Oversight and Investigations. U.S. House of Representatives Commitee on Commerce. Sep. 26, 1996. Re: Consumer Access to Home Testing Services and Devices.
Diabetes Interview—The Newspaper for the Diabetes Community, Issue No. 50, Sep. 1996.
PR News Wire Article, Nov. 26, 1996.

*Primary Examiner*—Eric F. Winakur
(74) *Attorney, Agent, or Firm*—Calfee, Halter & Griswold LLP

(57) ABSTRACT

A glucose measuring device for determining the concentration of glucose in intravascular blood within a body part of a subject. The device includes at least one light source having a wavelength of 650, 880, 940 or 1300 nm to illuminate the fluid. At least one receptor (14) associated with the light source (12) for receiving light and generating a transmission signal representing the light transmitted is also provided. A support piece is including for supporting the light source associated with the respective receptor. The support piece is adapted to engage a body part of a subject. Finally, a signal analyzer determines the glucose concentration in the blood of the subject. A method for determining the glucose concentration is also provided which calibrates a measuring device and sets the operating current for illuminating the light sources during operation of the device. Once a transmission signal is generated by receptors (14) receiving light via the light source and illuminated blood, and the high and low values from each of the signals are selected and stored in the device (20), the values are subtracted to obtain a single transmission value for each of the light sources. These calculated values are then compared to a database of target transmission values, either using a neural network, or directly compared to determine the glucose concentration, which value is then displayed (28) on the device.

28 Claims, 7 Drawing Sheets

U.S. PATENT DOCUMENTS

| | | | |
|---|---|---|---|
| 5,009,230 A | 4/1991 | Hutchinson | |
| 5,028,787 A | 7/1991 | Rosenthal et al. | |
| 5,063,531 A | 11/1991 | Kawai et al. | |
| 5,070,847 A | 12/1991 | Akiyama et al. | |
| 5,086,229 A | 2/1992 | Rosenthal et al. | |
| 5,183,042 A | 2/1993 | Harjunmaa et al. | |
| 5,204,532 A | 4/1993 | Rosenthal | |
| 5,222,495 A * | 6/1993 | Clarke et al. | 600/322 |
| 5,243,983 A | 9/1993 | Tarr et al. | |
| 5,267,152 A | 11/1993 | Yang et al. | |
| 5,313,941 A | 5/1994 | Braig et al. | |
| 5,360,004 A | 11/1994 | Purdy et al. | |
| 5,361,758 A | 11/1994 | Hall et al. | |
| 5,379,764 A | 1/1995 | Barnes et al. | |
| 5,383,452 A | 1/1995 | Buchert | |
| 5,398,681 A | 3/1995 | Kupershmidt | |
| 5,433,197 A | 7/1995 | Stark | |
| 5,448,992 A | 9/1995 | Kupershmidt | |
| 5,460,177 A | 10/1995 | Purdy et al. | |
| 5,515,847 A | 5/1996 | Braig et al. | |
| 5,529,755 A | 6/1996 | Higashio et al. | |
| 5,533,509 A | 7/1996 | Koashi et al. | |
| 5,551,422 A | 9/1996 | Simonsen et al. | |
| 5,579,232 A | 11/1996 | Tong et al. | |
| 5,910,109 A * | 6/1999 | Peters et al. | 600/316 |

* cited by examiner

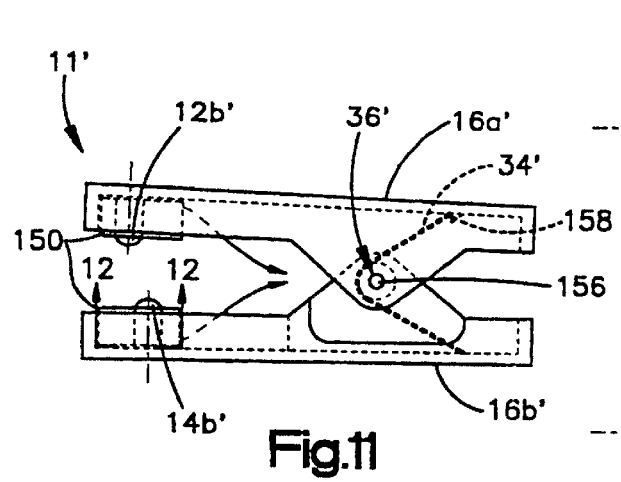
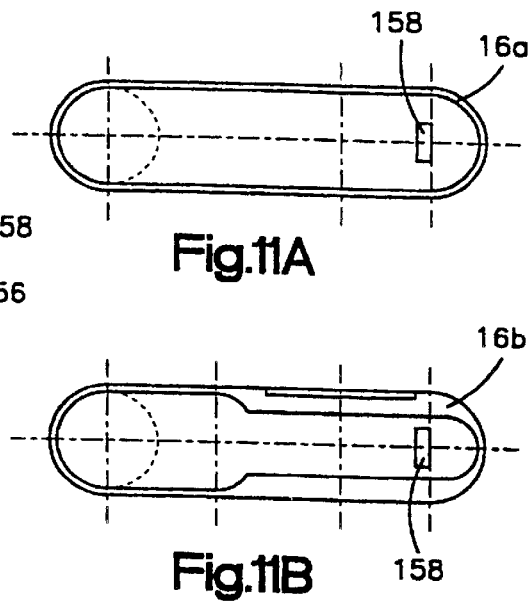
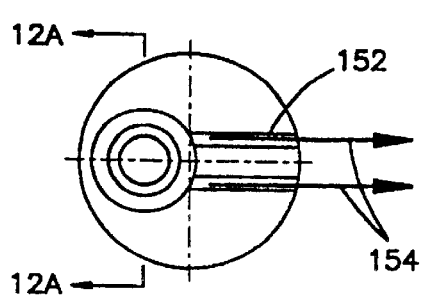
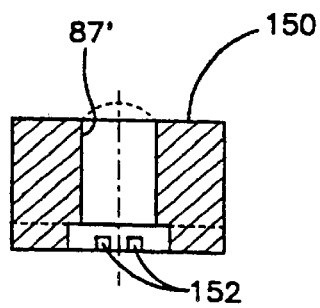
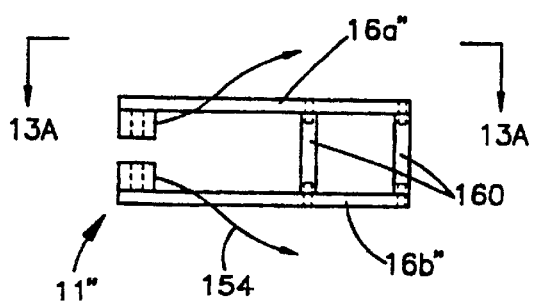
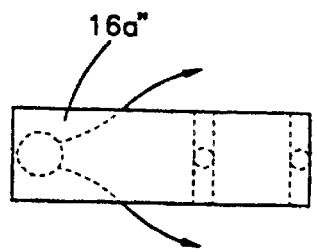

NON-INVASIVE GLUCOSE MEASURING DEVICE AND METHOD FOR MEASURING BLOOD GLUCOSE

Applicant hereby claims priority to PCT application PCT/US97/08852, filed Jun. 5, 1997, and this application is a continuation-in part of Ser. No. 08/803,066 U.S. Pat. No. 5,910,109 filed Feb. 20,1997.

TECHNICAL FIELD

The present invention relates generally to a medical diagnostic measurement instrument, and, more specifically, to a device and method for obtaining non-invasive quantitative measurements of blood glucose in patients.

BACKGROUND

The frequent monitoring of blood glucose levels in individuals with diabetes mellitus has become a major factor in the care of such patients over the past decade. Currently, it is possible for the diabetes patient and health care professionals to measure and record blood glucose levels using a variety of portable devices. Due to the need for multiple daily measurements, invasive blood for samples are a burden on the patient and often expensive. As a result, non-invasive devices using spectroscopic techniques, and which are battery powered and use solid-state electronics, have begun to be commercialized. Used at home, these devices allow diabetes patients to monitor and respond to fluctuations in blood glucose on a daily basis.

One example of such a device is disclosed in U.S. Pat. No. 5,070,874 to Barnes, et al. ("the '874 patent"). As set forth in the '874 patent, human blood glucose concentration levels vary greatly, and are found within the range of 0–600 milligrams per deciliter (mg/dl). Normal human blood glucose levels are in the approximate range of 80–110 mg/dl. Devices of the type disclosed in the '874 patent involve measurement of blood components using near infrared radiation and spectroscopic absorption techniques. Additional devices of this type are disclosed in U.S. Pat. Nos. 5,379,764 and 4,882,492, as well as numerous others, which make use of both reflectance and transmission spectroscopic analysis techniques.

Problems with these prior art devices have resulted due to several issues. One problem is the overlap of the spectrum of glucose with other blood sugars and chemicals. Another relates to hemoglobin-glucose binding, which renders discrete spectral measurements difficult. Also, spectroscopic techniques are typically unable to discriminate between sugars that are metabolized and those that are excreted, resulting in erroneous readings. Still further, prior art devices have failed to address issues which directly impact the accuracy of the measurements taken, such as the spectral effect produced by the skin and tissue, as well as variable blood vessel and skin thickness and composition.

As a result of these and other problems, the repeatability and resulting accuracy of such devices has not been in the range it is desired. The U.S. Food and Drug Administration is currently advising that non-invasive glucose measuring devices should have an accuracy in the range of 15% error or less.

SUMMARY OF THE INVENTION

According to the present invention, a transmission glucose measuring device is provided which uses a signal sensor assembly to illuminate intravascular blood or fluid components in the body. The assembly includes near infrared light sources on an external surface of a translucent body to illuminate blood or fluid, and light receptors positioned on an opposite external surface of the same body, to receive respective signals representing the radiation transmittance through the tissue and blood or fluid components illuminated. In the preferred embodiment one (1) light source emitting near infrared light of approximately 940 nm wavelengths is used. Alternatively, additional light sources, from two (2) to four (4) light sources, may be used emitting near infrared and infrared light between preferably 640 and 1330 nm, more preferably 650 and 1300 nm wavelengths. A fifth (5) possible light source may also be used, which would repeat one of the previous four (4) wavelengths. The light sources in the preferred embodiment are light emitting diodes (LEDs) which are pulsed at 1 kiloHertz (kHz) for a 1 millisecond (ms) pulse width. Where more than one receptor, or sensor, is used, each operates at a time when the other receptors are off to avoid further noise and signal contamination. The LEDs and opposite receptors are mounted on a biased or spring biased support for convenient attachment of the LEDs and receptors to the body part. In the preferred embodiment, a spring biased support is used for mounting on external surfaces of the human ear. The range of pressure applied to the ear by such supports and the associated LEDs and receptors should be no more than 15–30 mm of mercury (Hg), and is preferably much less, for example, 0.4 oz/square inch. It is understood that numerous shapes and configurations for the support could be used, depending on the shape of the body or body part to be measured.

Prior to use of the device, upon turning the device on a self-check is performed to ensure that all LEDs and respective receptors are operating to specification. Prior to use of the device, a calibration process is conducted to establish settings within the device which consider the skin or tissue and blood flow characteristics of the subject. Such calibration is believed to enable improved accuracy and predictability in glucose measurement in the present device, since factors such as tissue thickness and composition, as well as blood flow, are taken into consideration. Intensity calibration involves setting the intensity of the LEDs based on an LED intensity factor which is derived from the high and low data values measured from a pulse waveform signal.

The pulse of the subject is measured using an LED and its associated receptor to obtain the pulse waveform signal. The high and low blood flow data values collected to obtain the pulse waveform signal of the subject are converted and stored in a digital processor, such as an LED signal processor. Once the high and low pulse waveform signal values are known, the blood flow characteristics of the subject are used for the intensity calibration.

The intensity factor may be established based upon initial readings of the pulse waveform signal. Current is increasingly supplied to the LED to increase the intensity of the light source in a stepped fashion at one of multiple increments, until a minimally distorted desirable signal is received by the receptor. Once an acceptable signal is received, this selected level of LED intensity is stored by the processor, and becomes the level of current applied to each LED during operation of the device. Additionally, each LED is operated to determine that it is properly operational and that its respective receptor is receiving the LED's signal at the desired LED intensity. Alternately, the LED intensity factor may be established using a baseline voltage of approximately 1.2 volts. The LEDs are continuously checked by the device to ensure proper operation. In the event no signal is received, the device prevents a measurement from being taken and issues a warning notice to the operator.

Still another step in device calibration involves determining from the pulse waveform signal when measurements or readings should be taken by the device. Measurements of the LED signal are preferably only taken at a midpoint in the blood flow cycle, or at the "baseline" of the pulse waveform signal. For example, the difference between the high and low data values from the pulse waveform signal result in a value which is provided to the signal processor for establishing the timing of measurements, or signal generation, taken by the device with respect to the blood flow of the subject. Once the LED intensity factor and the baseline of the pulse waveform signal are determined, the device then initiates the operation and measurement of each of the LED signals, preferably through an ear lobe of the subject. Measurements from each LED are preferably taken several predetermined times, for example 30 seconds, at each of the high and low pulsatile values measured over 5 milliseconds, with the resulting sensor signal values stored and amplified in a sample and hold amplifier in the LED signal processor, converted in an analog-to-digital (A/D) converter, and normalized and averaged to obtain a single digital data value for each LED signal.

This pre-processed digital signal value from the LED signal processor is then provided to a further digital processor, preferably via a personal computer interface of the type well known to those of skill in the art. The digital processor is preferably a personal computer supporting conventional software and a database containing predetermined or target spectral glucose transmittance and absorbance data over a range of 0 to 600 mg/dl, for determining the glucose level of the subject from the digital signal value provided. Alternatively, a trained neural network containing the predetermined or target spectral glucose data may be used. The pre-processed digital signal value is incrementally compared to target data values in the database or "look-up table" to obtain a value which is slightly higher than the pre-processed signal value. Alternatively, the database could be used, and the comparison made in a trained neural network which is also well known to one of skill in the art. This closest incremental value, which is calculated by a linear interpolation between database values if no specific value is located within the database, is then provided to a digital display as the glucose level for review by the subject.

Other features and advantages the present device will become apparent from the following detailed description of the preferred embodiment made with reference to the accompanying drawings, which form a part of the specification.

BRIEF DESCRIPTION OF DRAWINGS

In the accompanying drawings, which are incorporated in and constitute a part of this specification, embodiments of the device described are illustrated, and together with the general description above, and the detailed description below, exemplify the device of the present invention.

FIG. 11 is a schematic side view of an alternate signal sensor assembly, or the support pieces for supporting a light source and receptor;

FIG. 11A is a partial, schematic bottom view of a first support piece for supporting the light source in the assembly shown in FIG. 11;

FIG. 11B is a partial, schematic top view of a second support piece for supporting the receptor in the assembly shown in FIG. 11;

FIG. 12 is a schematic bottom view of an insert taken along the line 12—12 of FIG. 11, for supporting a light source or receptor;

FIG. 12A is an enlarged schematic, cut-away side view of an insert for supporting a light source or receptor in the assembly shown in FIG. 11;

FIG. 13 is a schematic side view of another alternate signal sensor assembly, or the support pieces for supporting a light source and receptor;

FIG. 13A is a schematic top view of the assembly taken along the line 13A—13A of FIG. 13.

DETAILED DESCRIPTION OF THE PREFERRED EMBODIMENTS

Figure 1:
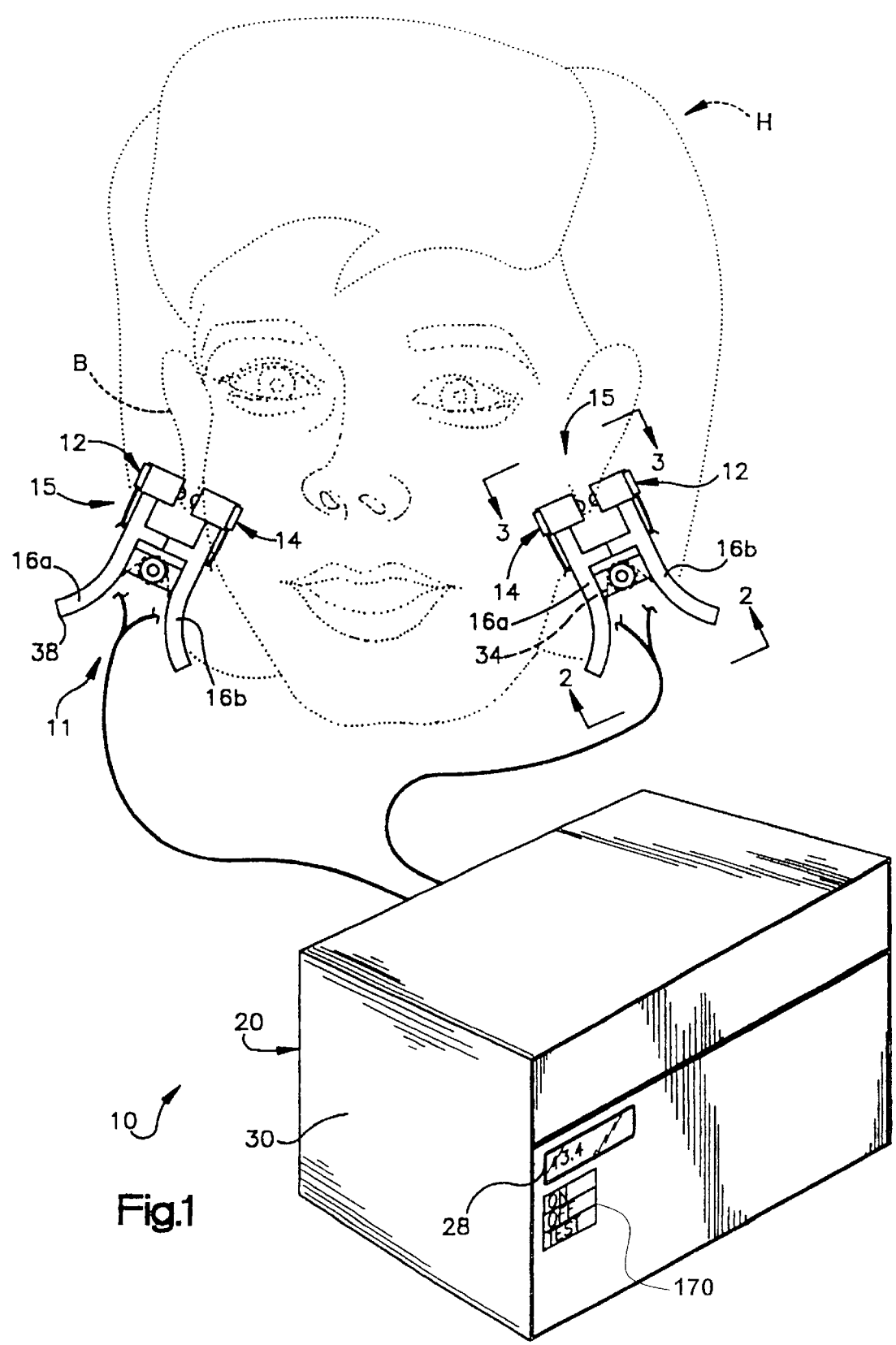
FIG. 1 is a schematic illustration of a transmission glucose measuring device as disclosed.
Figure 5:
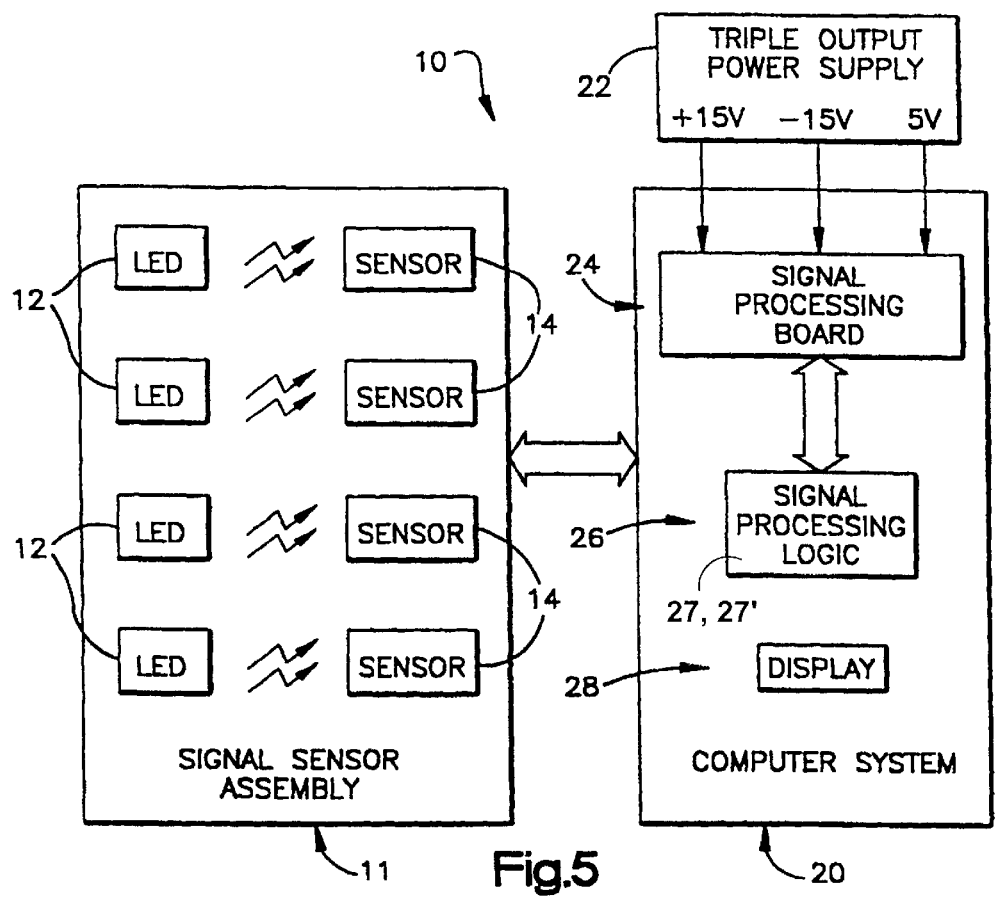
FIG. 5 is a high level block diagram of the present device showing a signal sensor assembly, triple output power supply and computer system.

FIG. 1 is a schematic illustration of the non-invasive transmission glucose measuring device 10 disclosed. The device includes a signal sensor assembly 11 comprising light sources or LEDs 12 and associated receptors 14 mounted on an assembly housing 15 comprising opposing spring biased support pieces 16. In the preferred embodiment, each support piece 16 has one or more LEDs 12 and associated receptors 14, for attachment to a body part B of a subject H. The device additionally includes a computer system 20 and a power supply 22 as shown in FIG. 5. The computer system 20 comprises a signal processing board 24, signal processing logic 26 and a display 28. The computer system components are housed within a black box or housing 30. The housing has dimensions of approximately 4 inches by 8 inches. The display 28 provides the glucose concentration measured and calculated by the present device for viewing by the user.

In the preferred embodiment, the signal sensor assembly 11 and its components, as shown in FIGS. 1 to 4, includes the support pieces 16 which are adapted for spring biased engagement surrounding portions of the human ear B. It is understood that other body parts such as the nose, fingers or toes could also be used. The first support piece 16a supports and is interconnected with the light sources 12, such that the LED is positioned to illuminate the surface of the ear as illustrated. The second support piece 16b supports and is interconnected with the receptors 14 associated with each LED, and are positioned opposite from their respective LEDs for receiving light transmitted from the LED through the ear B.

Figure 4:
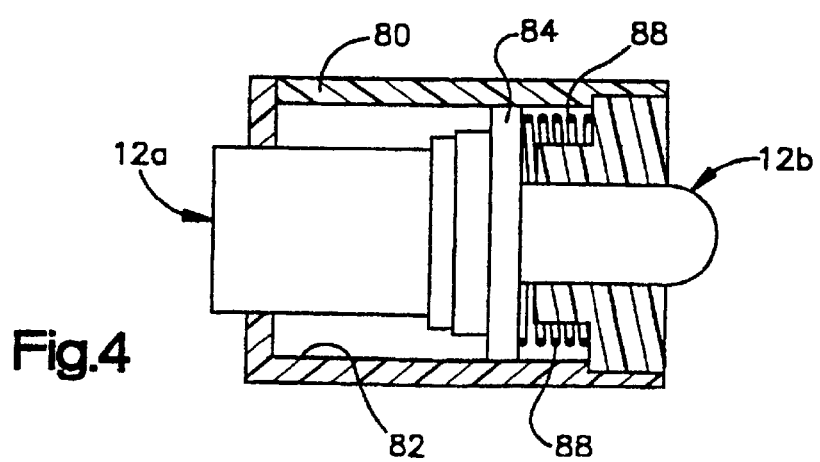
FIG. 4 is a schematic cut-away view of the support piece for supporting the light sources and associated receptors taken along the line 4—4 of FIG. 3.

In one illustrated embodiment, 4 or 5 LEDs emitting near infrared and infrared light at wavelengths of approximately 650, 880, 940 and 1300 nm, with a fifth possible light source used to repeat one of the previous four wavelengths. In the preferred embodiment a single LED and associated light source are used, with the LED having a wavelength of approximately 940 nm. The LEDs are pulsed at 1 kiloHertz (kHz) for a 1 millisecond (ms) pulse width. The LEDs include a housing portion 12a and a bulb portion 12b. The conventional LEDs are available from Optoelectronics of Sunnyvale, Calif. The conventional receptors 14 generating the transmission signals through the body part also include a housing portion 14a and a sensor portion 14b. The receptors are also available from Optoelectronics. Where combinations of LEDs and receptors are used, each combination of LED and receptor operate at a time when the others pair or pairs are off to avoid further noise and signal contamination. The LED housing 12a and bulb portion 12b is more fully shown in FIG. 4. It should be understood that the receptor housing 14a and bulb portion 14b, is identical in its support structure, such that no further discussion is required. As shown in FIGS. 1 and 4, the first and second support pieces 16a, 16b include an additional support body 80 for receiving the LED or receptor housing portions 12a, 16a. The support body 80 may be manufactured of any rigid polymer material, such as Delrin®. The support body 80 includes an opening 82 for receiving the LED or receptor housing portion 12a, 14a. At the end of the housing portions 12a, 14a, a floating support plate 84 is provided which is engaged with the bulb portion 12b, 14b and is movable with respect to the housing portion 12a, 14a. Additionally, an end fitting 86 is provided which is in press fit engagement with the support body opening 82, and includes a bulb opening 87 for receiving the bulb portion 12b, 14b, of the LEDs and receptors. Intermediate the end fitting 86 and the floating support plate 84, compression springs 88 are provided. In this arrangement, the bulb portion 12a, 14a of the LEDs and receptors are movable with respect to the support body 80, such that the bulb portions are in light spring biased or in floating engagement with the body B once they are in communication with the subject H.

Figure 2:
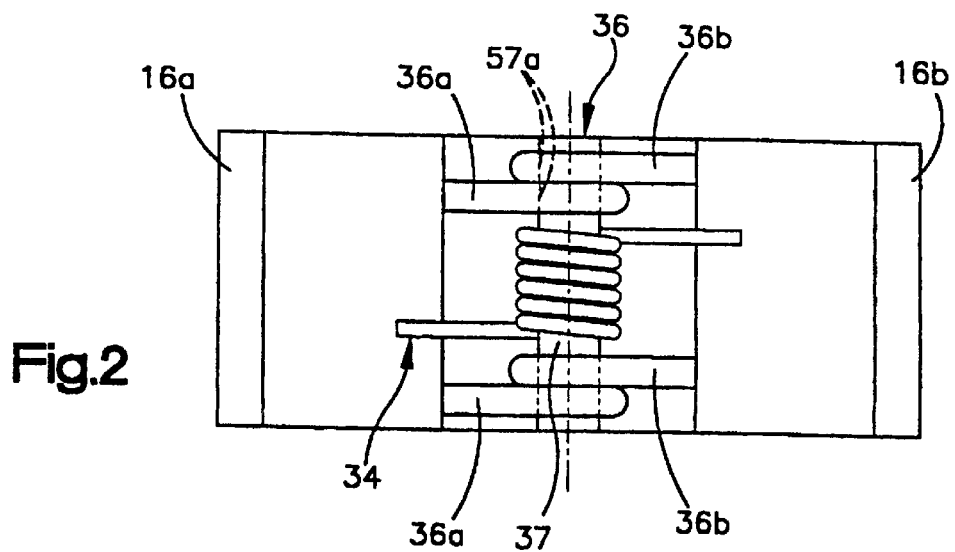
FIG. 2 is a schematic rear end view of a signal sensor assembly, or the support pieces for supporting the light sources and receptors, taken along the line 2—2 in FIG. 1.
Figure 3:
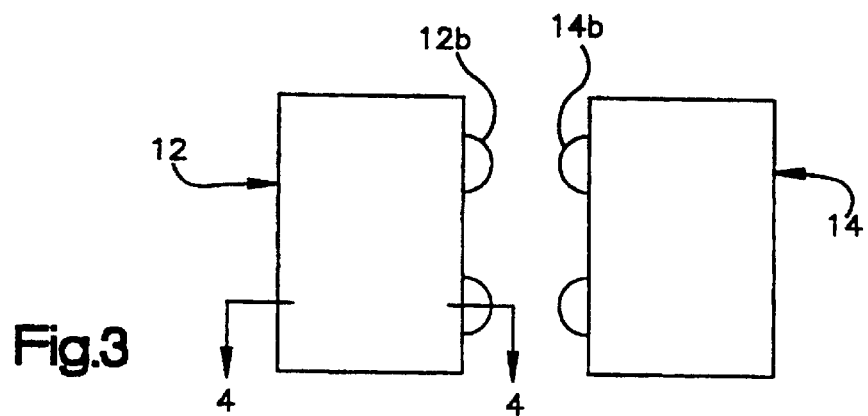
FIG. 3 is a schematic front end view of the support pieces for supporting the light sources and receptors taken along the line 3—3 in FIG. 1.

As shown in FIGS. 1 and 2, the support pieces 16a, 16b, or first and second plates which comprise the support piece 16, are interconnected at a pivot point 36 positioned intermediate the support pieces, and include a torsion spring 34 for biasing the support pieces toward one another. Legs 36a, 36b are interconnected with the support pieces 16a, and 16b, respectively, and are engaged through an opening 37a in the legs by an axle 37 for pivoting motion about the pivot point 36. Thus, the support pieces 16a, 16b, are manually moved toward one another on first ends 38 spaced from the end of the support pieces with the LEDs and receptors 12, 14, to provide a space between the LEDs and receptors for the ear, as shown in FIG. 1. Once the assembly 11 is positioned with one of each of the support pieces 16a, 16b on either side of the body part, the first ends 38 are gradually released to engage the LEDs and receptors with the body part.

As described here and shown in the preferred embodiment, the signal sensor assembly 11 operates in a manner similar to a spring biased clothes pin for securing clothing to a clothes line. It is particularly noted that the spring 34 must have a sufficient force to engage both the LEDs and the receptors with the ear B, but that the spring force is not so great that the intravascular blood flow within the ear is impacted. As previously stated, the force applied should be no greater than 15–30 mm of Hg. In the preferred embodiment, the desired pressure or spring pressure is approximately 0.4 oz/square inch.

It is also important to note that the arrangement of the support pieces 16a, 16b, must be such that the LEDs and receptors are at all times during operation of the device, aligned or positioned opposite from one another to enable proper illumination and receipt of the light transmission through the body part B. Thus, it is contemplated that one may choose to use an alternate arrangement of the spring biased support pieces, for example, changing the spring 34 position to eliminate the pivot 36, and alternatively provide parallel movement of the each of the support pieces, with the axis of the spring transverse to the support pieces. Further alternate and preferred embodiments of a signal sensor assembly are illustrated in FIGS. 11–13. For ease of understanding, where the elements of the assembly are similar, they are referred to using the same name, but designated with additional prime designations. Still further it is noted that the spacing between the bulb portions 12b, 14b, 12b', 14b", 12b", 14b" of the LED and receptors is preferably approximately 3/8 to 3/32 inches. This spacing is believed to maintain an alignment of within approximately 10° from a center line of the bulb portions.

An alternate embodiment of a signal sensor assembly 11' is illustrated in FIGS. 11–12A. The first support piece 16a' and second support piece 16b' each support an insert 150 for supporting the LED or receptor housing portions 12a', 14a'. The inserts are press fit into engagement with the first and second support pieces 16a', 16b'. The insert includes a bulb opening 87' where the bulb portions 12b', 14b' of the LED and receptors project from the inserts 150. Wire channels 152 are provided for interconnecting the LED and receptor wires 154 with the computer system 20. The first and second support pieces 16a', 16b' are interconnected at a pivot point 36', by a pin 156. A torsion spring 34' of approximately 6–8 ounces spring pressure is used surrounding the pivot pin, and engages stop members 158 on an internal surface of each of the first and second support pieces to maintain the spring 34' in position.

In a still further embodiment of a signal sensor assembly 11" illustrated in FIGS. 13–13A, the use of a spring to bias the support pieces is eliminated. Instead, the first and second support pieces 16a", 16b" are of a somewhat flexible material, such as circuit board substrate, with the LED and receptor housing portions 12a", 14a" mounted by conventional means, such as adhesive, to the material. Rigid spacers 160 are positioned intermediate the first and second support pieces by conventional fasteners as illustrated. It should be understood that use of a sensor assembly of the design of FIG. 13 may not be capable of fitting the body part of all subjects, such that more than one size of assembly may be required. Additionally, as only the flexibility of the material of the support pieces 16a", 16" maintains the assembly 11" engaged with the ear, an additional support member is preferably used to maintain the assembly engaged with the ear. This support member, not illustrated, is simply a wire hook arrangement engaged on one end with the assembly 11", and with a hook end supported surrounding the ear of the subject. It is pointed out that the non-protruding arrangement of the bulb portions 12b', 12", 14b', 14b" of the embodiments of FIGS. 11 and 13 are believed preferable, as these bulb portions avoid pinching of the ear lobe, which limits blood flow, and thereby increase accuracy of the receptor reading. During repeated, successive tests using the present device, it has been determined that best results may be obtained by removing the signal sensor assembly between tests and to massage the body part being tested in order to ensure that there is sufficient blood flow to the part being tested. Maintaining the assembly 11, 11', 11" on the body part between tests tends to pinch the body part, somewhat inhibit blood flow, and thereby decrease accuracy.

As shown schematically in FIG. 5, the signal sensor assembly 11 is electrically interconnected with the computer system 20 to drive illumination of the LED 12, 12', 12" and to receive signals from the receptor 14, 14', 14" corresponding to the light transmitted through the ear for further processing and display. It should be understood that the present device may make use of one or more combinations of LED and receptor pairs for successful operation. The FIG. 5 high level block diagram of the present device shows the signal sensor assembly, triple output power supply and computer system. The triple output power supply 22 includes +15 volt, −15 volt and a +5 volt power supply outputs.

Figure 6:
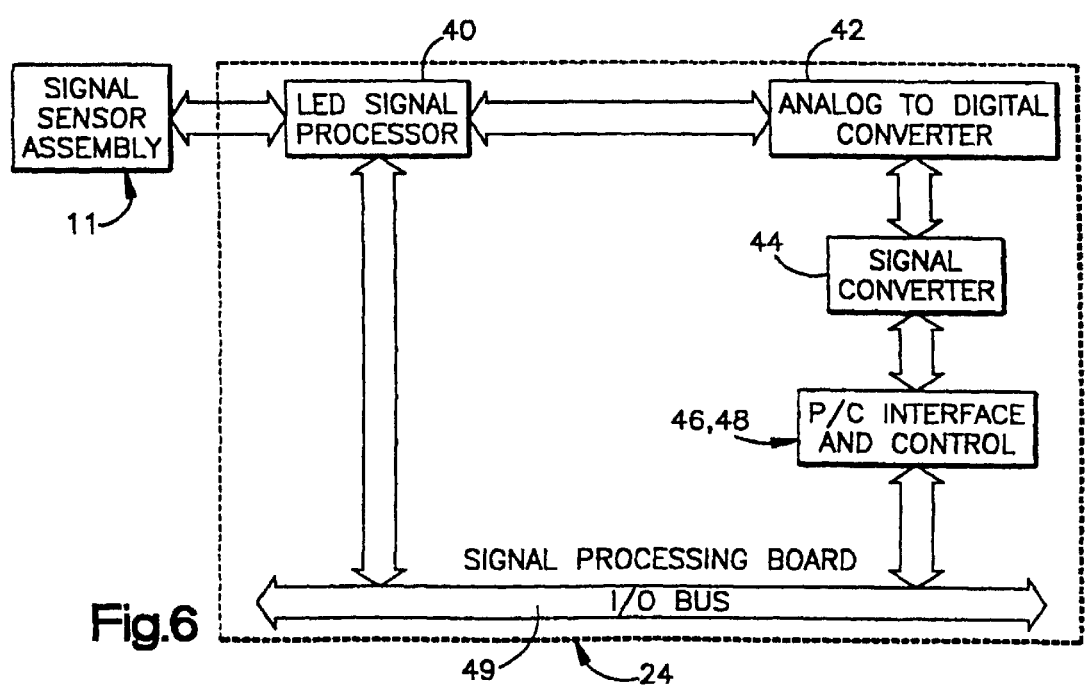
FIG. 6 is a high level block diagram illustrating the major components of a signal processing board of the present device.

As illustrated in FIG. 6 the major components of the signal processing board 24 include a LED signal processor 40, an analog-to-digital converter 42, a signal converter 44, a P/C interface 46 and a control circuit 48. Data is transferred between the signal processing board 24 and the P/C interface via an I/O bus 49. The P/C interface 46 of the preferred embodiment is a KB-8 PC-IN-A-Box from KILA of Boulder, Colo., or a 1×6×3 Compac, Inc. device. It should be understood that numerous conventionally available devices may be used. The illustrated conventional components are in circuit communication with each other as shown in FIG. 6. It should be noted in connection with the conventional A-to-D converter that additional known techniques are also used to enhance the signal to noise ratio such as the heterodyne detection scheme. This detection technique is well known to those of skill in the art and eliminates the DC offset problems caused by background illumination. Also, the use of coherent gating are used to improve the overall measurement accuracy since the measurement of interest is performed during a period of maximum blood flow. This technique enables the dwell time between the blood pulses to be used to obtain a measurement that yields a DC background value which can be subtracted from the peak value. This technique also eliminates measurement problems associated with tissue hydration, non-uniform tissue thickness and density, as well as patient to patient variation.

Figure 7:
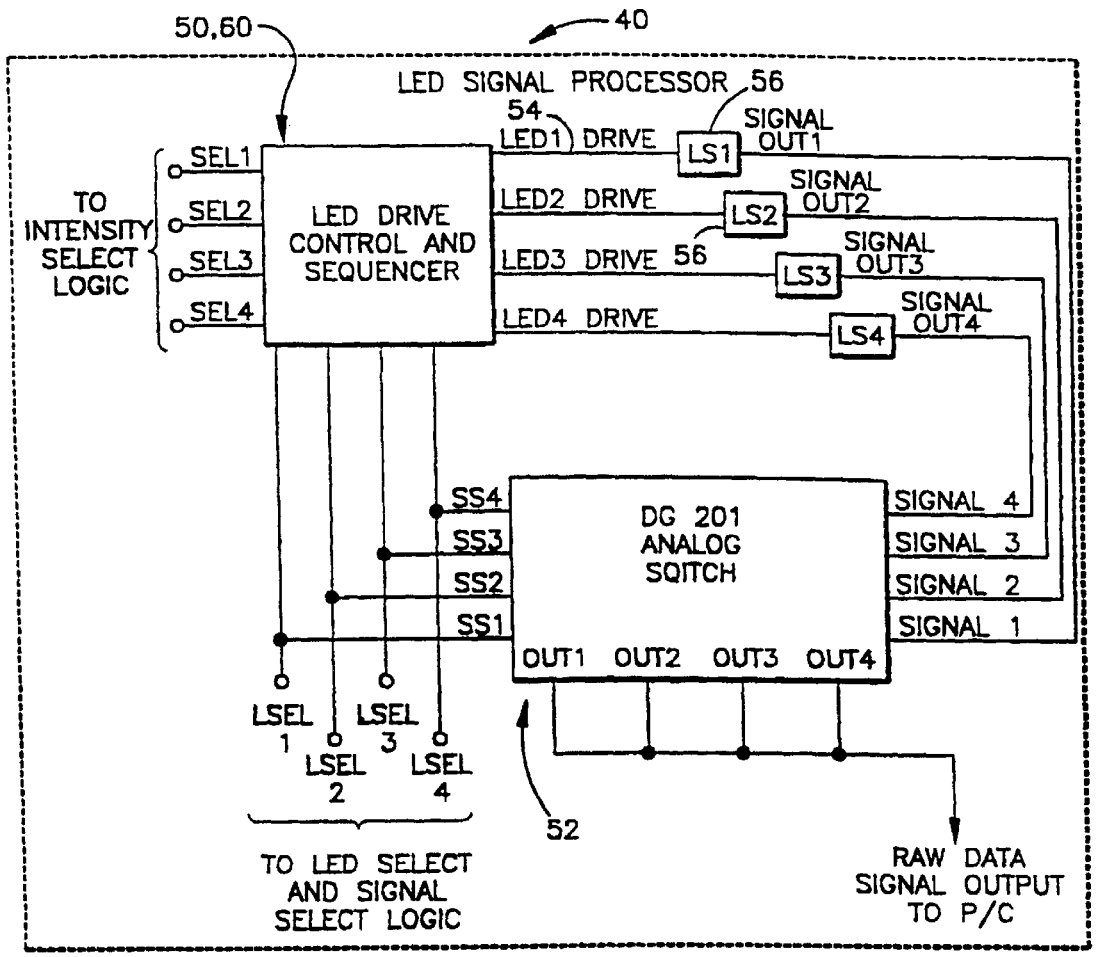
FIG. 7 is a block diagram of a LED signal processor of the present device.

Referring now to FIG. 7, a block diagram of the LED signal processor 40 of the present device is shown. The LED signal processor 40 includes a LED drive circuit 60 and sequencer circuit 50, an analog switch 52 and a plurality of connections 54 to a plurality of LED/sensor blocks 56 which are referenced as LS1, LS2, LS3 and LS4. The conventional components are in circuit communication with each other as shown in FIG. 7.

Figure 8:
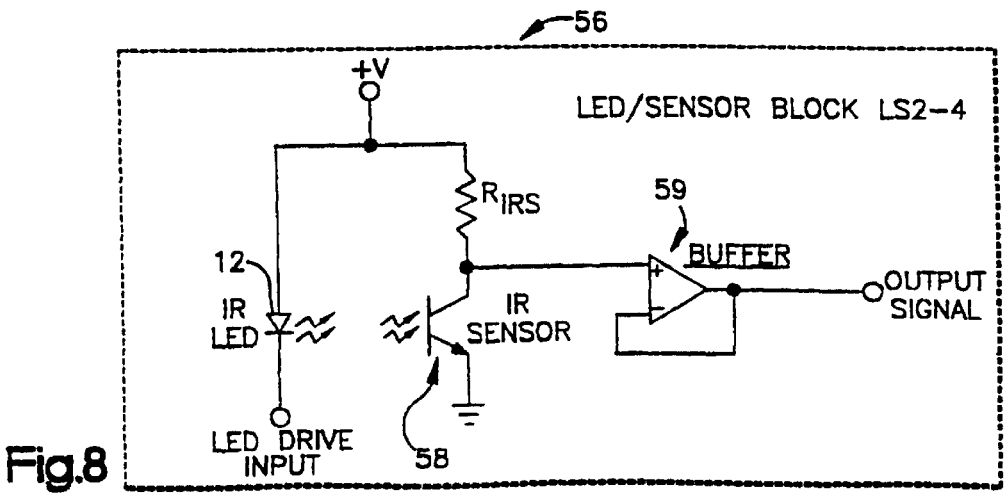
FIG. 8 is a schematic diagram of LED/sensor blocks LS1–LS4 of the present device.

Referring now to FIG. 8, a schematic diagram of LED/sensor blocks 56 or LS1-LS4 of the present device are illustrated. Each LED/sensor block 56 includes a LED 12, a sensor 58 and a buffer 59. These well known components are in circuit communication with each other as shown.

Figure 9:
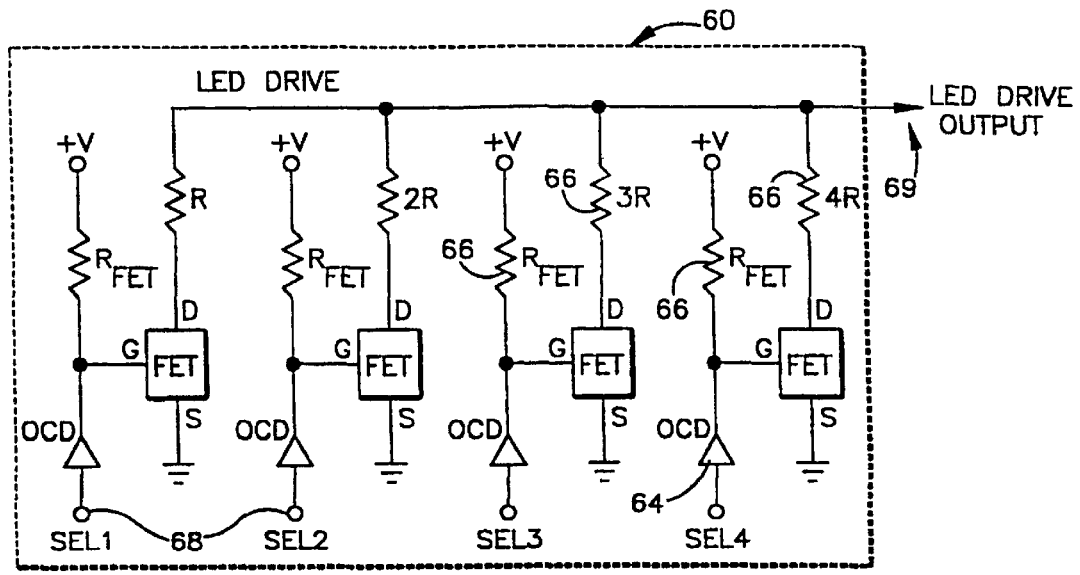
FIG. 9 is a schematic diagram of an LED drive circuit of the present device.

Illustrated in FIG. 9 is a schematic diagram of the LED drive circuit 60 of the present device. The LED drive circuit 60 includes a plurality of transistors (e.g. FET's) 62, drivers (e.g. OCD) 64 and a plurality of resistors (R, 2R, 4R, 8R and RFET) 66. The LED drive circuit 60 also includes inputs SEL1 through SEL4 68 and an output 69. The conventional circuit elements are in circuit communication with each other as shown.

Figure 10:
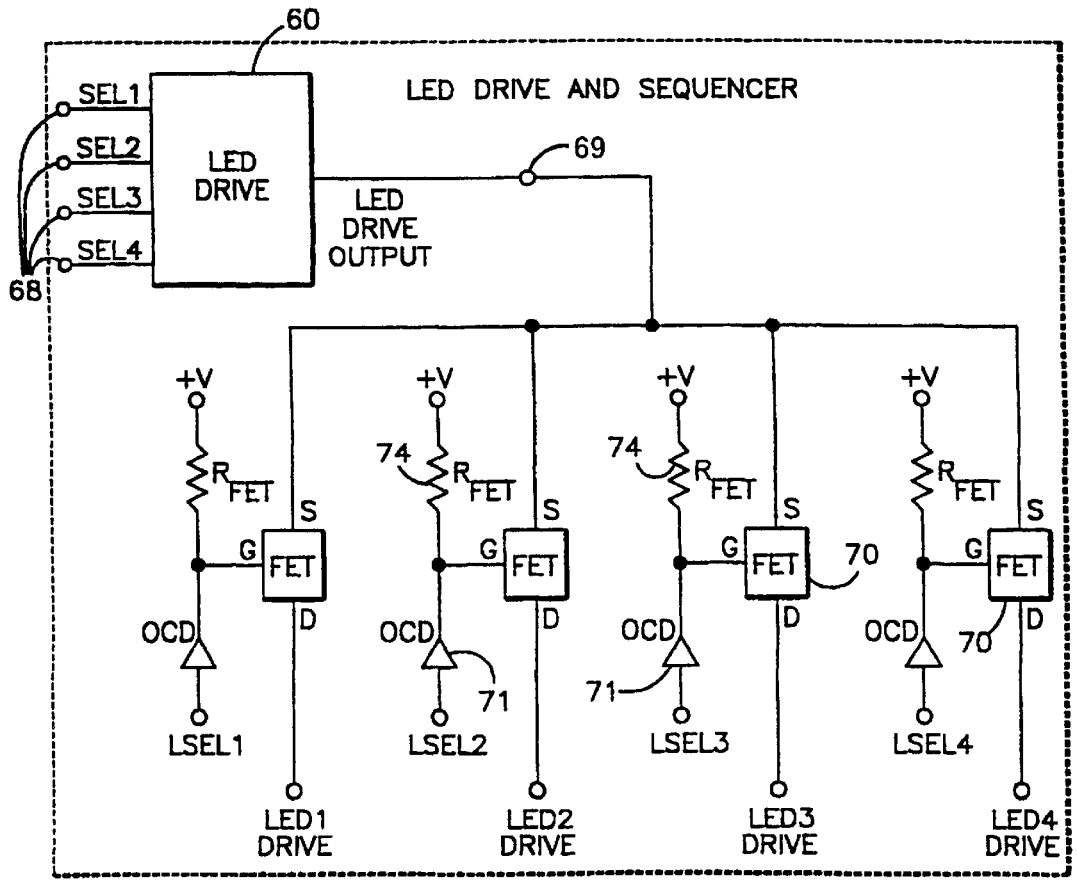
FIG. 10 is a block/schematic diagram of a LED drive and sequencer circuit of the present device.
Figure 14A:
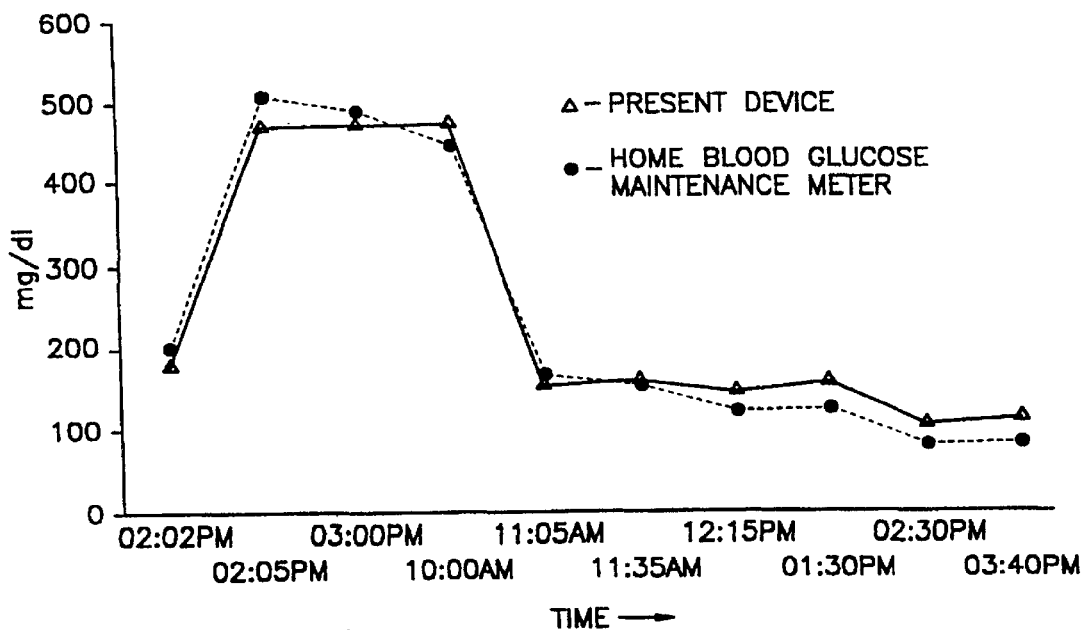
FIGS. 14A and 14B are graphic illustrations showing a comparison of the glucose concentration values determined by a prior art invasive blood glucose meter with the glucose concentration values obtained by the present device.
Figure 14B:
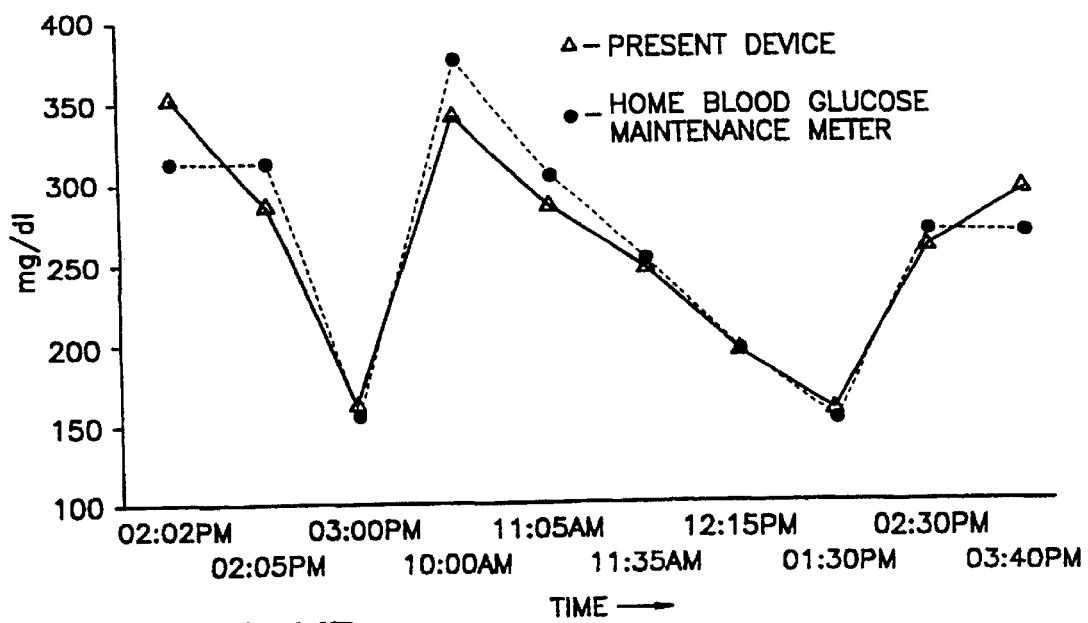

Illustrated in FIG. 10 is a block/schematic diagram of the LED drive 60 and sequencer circuit 50 of the present invention. The LED drive and sequencer includes the LED drive circuit 60 of FIG. 5, and a plurality of transistors (e.g. FET's)70, drivers (e.g. OCD) 71, and a plurality of resistors (R, 2R, 4R, 8R and $R_{FET}$) 74. In an alternate design, programmable resistors may be used. The LED drive 60 and sequencer circuit 50 also includes inputs LSEL1 through LSEL4, SEL1 through SEL4, and outputs LED1 DRIVE through LED4 DRIVE. The conventional circuit elements are in circuit communication with each other as shown.

The P/C interface 46 for the signal processing logic 26 may incorporate a conventional trained neural network 27 or, alternately, software making use of a database which conducts a linear evaluation and comparison of the tested signal with the signal values set forth in the database as described below 27', forming part of the signal processing logic which determines the measured glucose concentration based on a comparison of tile measured and pre-processed transmission signal with pre-determined spectral data stored in the neural network 27. Once calculated, the glucose concentration is provided to the display 28 mounted in the black box 30.

The conventional trained neural network 27, which is a standard back propagation network with a single hidden layer, allows the device to learn and discriminate between the target glucose substance from other blood components. Likewise, the preferred embodiment using a database or look-up table also contains target glucose values. In order to obtain the ideal or target glucose values over the spectral range of 700 to 1800 nm, tests were conducted on glucose dissolved in simulated blood. The simulated blood was i solution of 14.5% bovine hemoglobin and 5% albumin with synthetic noise in distilled water. These are the typical concentrations of hemoglobin and albumin found in human blood. The ideal spectra values were measured using a VIS/NIR spectrometer. The measured spectra were of simulated blood containing glucose concentrations in the range of 50 mg/dl to 600 mg/dl. Also, an empty curette data set was taken for reference, as sell as one albumin data set, one deionized water data set and seven hemoglobin data sets. An ideal measurement was taken without noise considerations, and a noisy measurement was taken which included a 5% noise component. During training of the neural network, adjustments are made to internal coefficients or weights until the network can predict the target value associated with each input to within a predetermined acceptable tolerance.

The preferred neural network or database would contain approximately 30–40 sets of target transmittance data corresponding to 30–40 different glucose levels. Set forth in Table 1 are the descriptions of the test substances:

TABLE 1

| Description | Concentration | N.N. Target | Training Output | Training Error | Test Output | Test Error |
|---|---|---|---|---|---|---|
| Glucose | 9% | 0.4 | 0.40191 | 0.5% | 0.4018 | 0.4% |
| Glucose | 18% | 0.5 | 0.49055 | 1.9% | 0.4882 | 2.4% |
| Glucose | 36% | 0.6 | 0.60116 | 0.2% | 0.6014 | 0.2% |

TABLE 1-continued

| Description | Concentration | N.N. Target | Training Output | Training Error | Test Output | Test Error |
|---|---|---|---|---|---|---|
| Albumin | | 0.3 | 0.29828 | 0.6% | 0.2939 | 2.0% |
| Deionized Water | | 0.2 | 0.20058 | 0.3% | 0.2005 | 0.2% |
| Hemoglobin | | 0.7 | 0.69965 | 0.0% | 0.6939 | 0.9% |
| Hemoglobin | | 0.72 | 0.71972 | 0.0% | 0.7159 | 0.6% |
| Hemoglobin | | 0.8 | 0.80149 | 0.2% | 0.7870 | 1.6% |
| Hemoglobin | | 0.82 | 0.81838 | 0.2% | 0.8112 | 1.1% |
| Hemoglobin | | 0.84 | 0.83949 | 0.1% | 0.8357 | 0.5% |
| Hemoglobin | | 0.86 | 0.86286 | 0.3% | 0.8526 | 0.9% |
| Hemoglobin | | 0.88 | 0.87260 | 0.8% | 0.8596 | 2.3% |
| Empty | | 0.1 | 0.09956 | 0.4% | 0.1004 | 0.4% |

The present device using the above-described components, including a database containing target transmission glucose values, is generally operated as follows. First, a self-check of the device is performed to confirm operation of the signal sensor assembly 11, including the LED 12 and associated receptor 14. Next, several calibration steps are performed to initialize the device. One such step is setting the intensity of the LED 12. This is determined based on the LED intensity factor. The LED intensity factor is measured based on the high and low data values measured from the pulse waveform signal taken from the pulse of the subject. The pulse of the subject may be taken on one of the LED 12 and associated receptors 14. Alternately, the pulse may be taken using any number of conventional methods, the results of which are collected and provided to the computer system 20. In the preferred embodiment, the high and low pulse data values are collected and used to obtain the pulse waveform signal which is converted from analog to digital and stored in the computer system 20 within the LED signal processor 40.

In both the neural network embodiment and the linear evaluation embodiment of the present device, an intensity factor is next established using the pulse waveform signal. During initialization of the device, current is increasingly and incrementally supplied to an LED 12 to increase the intensity of the light source. During collection of the signals the system offset point is increased to obtain approximately 0.2 volts, and the system gain point is increased to obtain approximately 6 volts. This stepped process is performed until a minimally distorted predetermined desirable signal is received by the associated receptor 14. Once an acceptable signal is received, the there operating level of LED intensity is stored by the LED signal processor 40, and becomes the current applied to the LED 12 during regular operation of the device. A baseline voltage for the signal sensor assembly 11, 11', 11" is also preferably used in both embodiments. The baseline voltage used is within a range of 1.2–2.3 volts. The baseline voltage is manually established by the user of the device. A generalized selection of the type of body part being tested is made by the user, based on the "thin," "average" or "heavy" nature of the subject. A series of buttons 170, or other manual selection device, is provided on the housing 30 which enables the setting of a system voltage setting according to the body type selected. The thin setting establishes the baseline voltage at approximately 1.2 volts. The average setting establishes the baseline voltage at approximately 1.5 volts, and the heaving setting establishes the baseline voltage at approximately 2 volts. In each of the embodiments, continuous checking of the LED and receptor are performed to ensure proper operation of the device is maintained at all times. A warning notice is provided to the operator in tile event improper operation is detected.

Next in the calibration process, the device calculates when measurements or readings should be taken by the device. Measurements of the LED signals are preferably only taken at a midpoint in the subject's blood flow cycle. This has been previously described as the positive "baseline" of the pulse waveform signal, which, in the present device, means the positive difference between the high and low data values from the pulse waveform signal. As these signals are stored within the LED/sensor blocks 58 within the signal processor 40, timing of the operation of the LEDs 12 is readily determined using the drive circuit 60 as indicated in FIGS. 7–10.

Once these initial operations are completed, the signal sensor assembly 11 is then operated at the times and increments calculated by and stored in the computer system 20, in particular the LED drive 60 and sequencer circuit 50, to measure each of the LED signals, all as indicated in FIGS. 7–10.

Measurements from each of the LEDs are taken several predetermined times at each of the high and low pulsatile values measured over 5 milliseconds, with the resulting sensor signal values amplified as described, where in the LED signal processor 40. In the neural network embodiment, the converted signals are averaged together to obtain a single digital data value for each of the LED signals.

The final signal value is then converted in the analog-to-digital converter 42. The pre-processed digital signal from the LED signal processor 40 is then provided to the signal processing logic 26 within the P/C interface 46 of the computer system 20 via the I/O bus 49 as illustrated in FIG. 6. The trained neural network 27 supported on the P/C interface compares the glucose transmittance data provided via the LED signal processor 40 with the predetermined or target spectral glucose transmittance data stored within the neural network, and upon finding a comparative value determines the glucose level of the subject from the digital signal provided.

In the linear evaluation embodiment 27' of the device, the high and low signal values stored are then normalized using computer software to finally adjust the signal values. A continuous comparison of the normalized transmission data or values is conducted to obtain the highest and lowest transmission values collected. To further improve the signal to noise ratio, the lowest value is then subtracted from the highest values to obtain a single calculated transmission value. This single calculated transmission value is then compared to the target data or the predetermined glucose values stored within the database or lookup table of the type used in the neural network embodiment, and previously described.

Upon successful comparison of the calculated transmission value with an equivalent target data value, by repeated comparisons between the calculated and target values, the equivalent selected glucose level is then provided to the digital display 28. Where the identical equivalent value is not found within the database, the next nearest points are located and a value is found by linear interpolation between the next nearest points. In the event additional operations of the device on the same subject are desired, tic subject preferably removes the sensor assembly, briefly massages the body part to ensure good blood flow, reattaches the assembly and manually selects the "test" button provided on the housing 30 to run another test. The device then repeats the entire process previously described, including initialization, since the support pieces of the assembly were moved, or some other problem may have occurred.

The preferred form of the glucose measuring apparatus 10 has been described above. However, with the present disclosure in mind it is believed that obvious alterations to the preferred embodiment, to achieve comparable features and advantages in other assemblies, will become apparent to those of ordinary skill in the art.

We claim:

1. A glucose measuring device for determining the concentration of glucose in fluid within a body part of a subject, comprising:
   a) at least one light source emitting near infrared or infrared light having a wavelength of between 640 and 1000 nm to illuminate the fluid, and at least one receptor associated with and opposite from said light source for receiving light emitted by said light source and transmitted through the fluid and body part of the subject and generating a transmission signal representing the light transmitted from said first light source;
   b) a support piece having a first plate for supporting said light source, and a second plate movable with respect to said first plate for supporting said receptor associated with said light source;
   c) said support piece adapted to place a body part of a subject intermediate said first and second plates and to illuminate the body part and fluid using said light source; and
   d) a signal analyzer interconnected with said receptor for receiving said transmission signal and for determining from the transmission signal the glucose concentration in the fluid within the illuminated body part.

2. The device of claim 1, wherein said light source has a wavelength of 940 nm.

3. The device of claim 1 or 2, further including a second light source emitting near infrared or infrared light having a second wavelength of either 650, 880, 940 or 1300 nm, which is different from the wavelength of said light source, to illuminate the fluid, and a second receptor associated with said second light source for receiving light emitted by said second light source and transmitted through the fluid and a body part of the subject and generating a second transmission signal representing the light transmitted from said second light source.

4. The device of claim 3, wherein said second light source has a wavelength of 880 nm.

5. The device of claim 4, further including a third light source emitting near infrared or infrared light having a third wavelength of either 650, 880, 940 or 1300 nm, which is different from the wavelengths of said light source and second light source, to illuminate the fluid, and a third receptor associated with said third light source for receiving light emitted by said third light source and transmitted through the fluid and a body part of the subject and generating a third transmission signal representing the light transmitted from said third light source.

6. The device of claim 5, wherein said third light source has a wavelength of 650 nm.

7. The device of claim 5, further including a fourth light source emitting near infrared or infrared light having a third wavelength of either 650, 880, 940 or 1300 nm, which is different from the wavelengths of said light source, second and third light sources, to illuminate the fluid, and a fourth receptor associated with said fourth light source for receiving light emitted by said fourth light source and transmitted through the fluid and a body part of the subject and generating a fourth transmission signal representing the light transmitted from said fourth light source.

8. The device of claim 7, wherein said fourth light source has a wavelength of 1300 nm.

9. The device of claim 7, further including a second support piece having a first plate for supporting said third and fourth light sources, a second plate movable with respect to said first plate for supporting said third and fourth receptors associated with their respective third and fourth light sources, and said second support piece adapted to place a body part of a subject intermediate said first and second plates of said second support piece and to alternately illuminate the body part and fluid using said third and fourth sources.

10. The device of claim 9, wherein said first and second plates of said support piece are spring biased to provide contacting engagement of said light source supported on said first plate with one side of the body part, and contacting engagement of said receptor supported on said second plate with an opposite side of the body part.

11. The device of claim 1, wherein said first and second plates of said support piece are spring biased to provide contacting engagement of said light source supported on said first plate with one side of the body part, and contacting engagement of said receptor supported on said second plate with an opposite side of the body part.

12. The device of claim 1, further providing a display monitor interconnected with said signal analyzer for displaying the glucose concentration determined.

13. The device of claim 12, Wherein said signal analyzer is a trained back propagation neural network with a single hidden layer.

14. The device of claim 13, wherein the fluid measured within the body part is intravascular blood and the body part is the ear.

15. A method for determining the glucose concentration in intravascular blood within a body part of a subject comprising the steps of:
   i) calibrating a non-invasive glucose measuring device by:
      a) measuring the pulse waveform of a subject;
      b) incrementally increasing an electrical current illuminating a first light source, incrementally reading a transmission signal generated in a corresponding first receptor associated with said first light source, said first receptor positioned adjacent to and engaging the body part on an opposite side of the body part from said first light source, and comparing incremental transmission signals until a predetermined desired quality of transmission signal is received from said first light source;
      c) establishing said electrical current which resulted in the desired quality of transmission signal as an operating current for illuminating said first light source during operation of said glucose measuring device;
   ii) operating said non-invasive glucose measuring device at said operating current by:
      a) illuminating intravascular blood within a body part using said first light source positioned adjacent to and engaging the body part, said light source having a wavelength of between 640 to 1330 nm and being illuminated at said operating current;
      b) generating a transmission signal in said first receptor from said first light source via the illuminated intravascular blood of the body part, said first receptor positioned adjacent to and engaging the body part on an opposite side of the body part from said first light source;
      c) storing high and low values from each of the multiple transmission signals from the light source;
      d) selecting a highest value from the transmission signals generated to obtain a highest transmission value for said light source;

e) selecting a lowest value from the transmission signals generated to obtain a lowest transmission value for said light source;

f) analyzing said highest and lowest transmission values to determine the glucose concentration in the intravascular blood within the body part; and g) displaying the glucose concentration.

16. The method of claim 15, wherein the step of measuring the pulse waveform of a subject comprises using said first light source for measuring the pulse waveform.

17. The method of claims 15 or 16, wherein the step of illuminating intravascular blood within a body part using said first light source positioned adjacent to and engaging the body part, uses a light source having a wavelength of 940 nm.

18. The method of claim 17, further comprising the step of illuminating intravascular blood within a body part using a second light source positioned adjacent to and engaging the body part and emitting near infrared or infrared light having a second wavelength of either 650, 880, 940 or 1300 nm, which is different from the wavelength of said first light source, to illuminate the fluid, and generating a transmission signal in a second receptor, said second receptor associated with said second light source for receiving light emitted by said second light source and transmitted through the fluid and body part of the subject, representing the light transmitted from said second light source.

19. The method of claim 18, wherein the step of illuminating intravascular blood within a body part using said first and second light sources is performed alternately, such that only one light source is illuminated at any one time.

20. The method of claim 19, further comprising the steps of selecting the highest and lowest values from the transmission signals generated to obtain a high and low transmission value from said second receptor, averaging the high and low values from said transmission signals for said second light source, analyzing the averaged transmission signals to determine the glucose concentration in the intravascular blood within the body part, and displaying the glucose concentration.

21. The method of claim 20, wherein the step of analyzing the highest and lowest transmission values by subtracting the lowest transmission value from the highest transmission value and selecting a comparable value or interpolating between the closest values from predetermined glucose transmission values to determine the glucose concentration.

22. The method of claim 17, wherein the step of analyzing the highest and lowest transmission values by subtracting the lowest transmission value from the highest transmission value and selecting a comparable value or interpolating between the closest values from predetermined glucose transmission values to determine the glucose concentration.

23. A glucose measuring device for determining the concentration of glucose in fluid within a body part of a subject, comprising:

a) a light source consisting essentially of a single light source emitting near infrared or infrared light having a wavelength of between 640 and 1330 nm to illuminate the fluid, b) at least one receptor associated with and opposite from said light source for receiving light emitted by said light source and transmitted through the fluid and body part of the subject and generating a transmission signal representing the light transmitted;

c) a support piece having a first plate for supporting said light source, and a second plate movable with respect to said first plate for supporting said receptor associated with said light source;

d) said support piece adapted to place a body part of a subject intermediate said first and second plates and to illuminate the body part and fluid using said light source; and e) a signal analyzer interconnected with said receptor for receiving said transmission signal and for determining from the transmission signal the glucose concentration in the fluid within the illuminated body part.

24. The device of claim 23, wherein said light source has a wavelength of approximately 940 nm.

25. The device of claim 23, wherein said first and second plates of said support piece are spring biased to provide contacting engagement of said light source supported on said first plate with one side of the body part, and contacting engagement of said receptor supported on said second plate with an opposite side of the body part.

26. The device of claim 24, wherein the fluid measured within the body part is intravascular blood and the body part is the ear.

27. The device of claim 23, further providing a display monitor interconnected with said signal analyzer for displaying the glucose concentration determined.

28. The device of claim 27, wherein said signal analyzer is a trained back propagation neural network with a single hidden layer.

* * * * *